United States Patent
Moussa et al.

(10) Patent No.: US 7,217,530 B2
(45) Date of Patent: May 15, 2007

(54) PROCESS FOR DETECTING PRP USING A MACROCYCLIC ADJUVANT LIGAND

(75) Inventors: Aly Moussa, Oullins (FR); Anthony William Coleman, Calluire-Et-Cuire (FR); Patrick Shahgaldian, Lyons (FR); Eric Da Silva, Lyons (FR); Ambroise Martin, Charly (FR); Adina Nicoleta Lazar, Lyons (FR); Edwige Leclere, Lyons (FR); Marilyne Dupin, Vaugneray (FR); Herve Perron, Saint-Genies-les-Ollieres (FR)

(73) Assignees: Agence Francaise de Securite Sanitaire des Aliments-AFSSA (FR); Centre National de la Recherche Scientifique-CNRS (FR); Universite Claude Bernard Lyon and Biomerieux (FR)

( * ) Notice: Subject to any disclaimer, the term of this patent is extended or adjusted under 35 U.S.C. 154(b) by 0 days.

(21) Appl. No.: 11/148,945

(22) Filed: Jun. 9, 2005

(65) Prior Publication Data

US 2006/0019311 A1    Jan. 26, 2006

Related U.S. Application Data

(63) Continuation of application No. PCT/FR03/03857, filed on Dec. 19, 2003.

(30) Foreign Application Priority Data

Dec. 20, 2002  (FR)  .................................. 02 16383

(51) Int. Cl.
*G01N 33/53* (2006.01)
*G01N 33/551* (2006.01)
*G01N 33/547* (2006.01)
*C12Q 1/37* (2006.01)
*C07K 1/04* (2006.01)

(52) U.S. Cl. .................. 435/7.1; 435/7.92; 435/23; 435/961; 436/524; 436/532; 436/823; 530/403; 530/807

(58) Field of Classification Search ............... 435/7.1, 435/7.92, 961, 23; 530/403, 807; 436/524, 436/532, 823
See application file for complete search history.

(56) References Cited

U.S. PATENT DOCUMENTS 5,571,911 A    11/1996  Still et al.
5,891,641 A *  4/1999  Prusiner et al. .............. 435/7.1

FOREIGN PATENT DOCUMENTS

| WO | WO 97/37995    | 10/1997 |
| WO | WO 01/23425 A1 | 4/2001  |
| WO | WO 01/77687 A2 | 10/2001 |
| WO | WO 02/086511 A2| 10/2002 |

* cited by examiner

*Primary Examiner*—Long V. Le
*Assistant Examiner*—Shafiqul Haq
(74) *Attorney, Agent, or Firm*—DLA Piper US LLP

(57) ABSTRACT

A process for detecting the forms of the prion pathogens responsible for subacute, transmissible, spongiform encephalopathies, including a macrocyclic adjuvant ligand (AML), free or bound to a support, that is added to a biological sample capable of containing $PrP^{sc}$, the resulting suspension then being reacted with an anti-$PrP^{sc}$ antibody, and the presence of PrP is then detected.

9 Claims, 11 Drawing Sheets

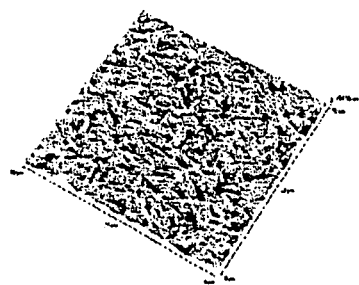 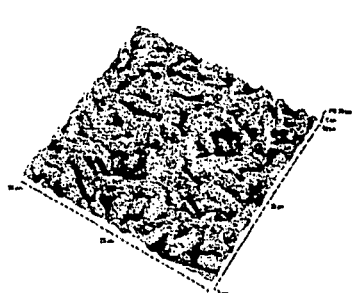 
Figure 3 A        Figure 3 B        Figure 3 C
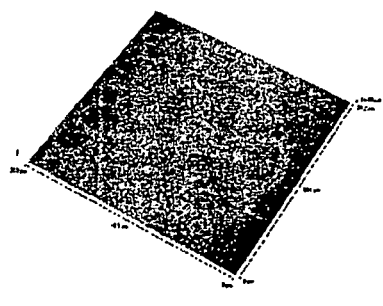 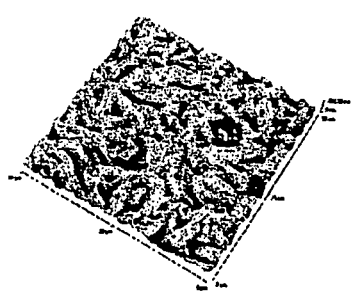 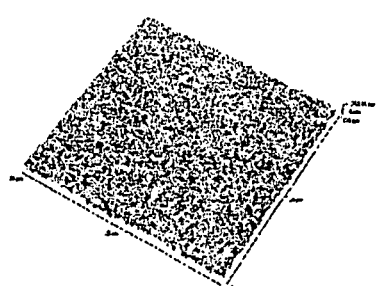
Figure 4 A        Figure 4 B        Figure 4 C continues from previous page …

PROCESS FOR DETECTING PRP USING A MACROCYCLIC ADJUVANT LIGAND

RELATED APPLICATION

This is a continuation of International Application No. PCT/FR2003/003857, with an international filing date of Dec. 19, 2003 (WO 2004/059322 A1, published Jul. 15, 2004), which is based on French Patent Application No. 02/16383, filed Dec. 20, 2002.

FIELD OF THE INVENTION

This invention relates to a process for detecting the forms of prion pathogens responsible for subacute, transmissible, spongiform encephalopathies.

BACKGROUND

The native or normal prion protein, designated PrP or $PrP^c$, for the cellular prion protein is a glycoprotein broadly expressed in the lymphoid and neuronal cells of mammals.

Conformational changes of $PrP^c$ result in the appearance and the propagation of the protein pathogen $PrP^c$, that is resistant to the proteinase K. This protein pathogen can be indifferently called $PrP^{sc}$ or $PrP^{res}$. Accumulation of $PrP^{sc}$ in the organs of animals is at the origin of numerous diseases and especially trembling in small ruminants, of chronic cachetic disease (or chronic wasting disease "CWD") of the elk and antelope, bovine spongiform encephalopathy (ESB) and Creutzfeld-Jakob disease (MCJ) in humans.

The delayed appearance after an incubation period of 2 to 6 years and the slow development of symptoms in cattle infected with ESB has considerably slowed the development of epidemiological models. ESB is transmissible by ingestion to humans and has resulted in the appearance of a new form of Creutzfeld-Jakob disease (vMJC).

Detecting the protein pathogen $PrP^{sc}$ is difficult in infected animals that are otherwise healthy before the development of the disease and especially in the blood and urine of diseased animals. It has been established that $PrP^{sc}$ present in animals intended for human consumption is transmitted to humans during the ingestion of infected tissues. Thus, a major objective of public health is to avoid this transmission by detecting the presence of $PrP^{sc}$:

In animals intended for human consumption to remove them from the food chain;

In blood donations and blood derivatives intended for transfusion to humans. In fact, as the presence of the protein pathogen $PrP^{sc}$ in the blood and the lymphoid liquids shows well before the cerebral disturbance, and thus well before the possibility of detecting the neurological signs suggestive of a clinically declared prion disease, the physiopathology in humans is poorly recognized and, not being able to carry out experimental infections as in sheep, the absence of a detection test in the blood or another biological fluids does not allow it to be studied and to thus prevent human to human transmission by blood donation or to treat infected persons before the cerebral lesions have begun; and In animal herds before the neurological stage, thus permitting the elimination of animals infected early before their arrival in the slaughterhouse.

Detecting the presence of $PrP^{sc}$ in biological samples or animals has thus become extremely important and several research teams are developing methods of immunological detections (WO 02/086551). Moreover, methods of complexing peptides, small molecules or inhibittors to $PrP^{sc}$ to treat vMJC constitute the subject of active research. However, those methods constantly come up against the difficulty of identifying $PrP^{sc}$ in a reliable manner when it is in a low quantity in a biological sample and especially in biological fluids.

SUMMARY OF THE INVENTION

This invention relates to a process for detecting PrP including adding a macrocyclic adjuvant ligand (AML) that is free or linked to a support to a biological sample capable of containing PrP; reacting a resulting suspension with an anti-$PrP^{sc}$ antibody; and identifying the presence of PrP.

This invention also relates to the process wherein the macrocyclic adjuvant ligand corresponds to the general formula (I) below:

(I)

[Structure showing a benzene ring with substituents $R_1$, $R_2$, $R_3$, $R_4$, $R_5$, $R_6$, linked to Y and $X_m$ group, with subscript n]

in which $R_1$ represents a hydrogen atom, a hydroxyl group, an OR group or an OCOR group with R as defined below, $R_2$ represents a hydrogen atom, a group R, COR, Pol, $CH_2Pol$ in which Pol represents a phosphate, sulfate, amine, ammonium, carboxylic acid group and R is as defined below, $R_3$ represents a hydrogen atom, a hydroxyl group, an OR group or an OCOR group in which R is as defined below, $R_4$ represents a hydrogen atom, a hydroxyl group, an OR group, an $OCH_2R$ group or an OCOR group in which R is as defined below, Y is an atom of carbon, nitrogen or an atom of sulfur, $R_5$ and $R_6$ are, each independently, absent or represent a hydrogen atom, a $CH_2$ group or R as defined below, or $R_5$ and $R_6$ together represent an atom of oxygen or of sulfur, X represents a $CH_2$ group or an atom of oxygen or of sulfur, m represents a positive integer equal to 0 or 1, R represents a hydrogen atom or a hydrocarbon chain, saturated or unsaturated, branched or unbranched, cyclic or non-cyclic, substituted or not substituted by a halogen group and carrying polar or non-polar functions, n is a positive integer between 3 and 15, and $R_1$ to $R_5$, R, X, Y and m can be different.

This invention further relates to the process wherein the macrocyclic adjuvant ligand corresponds to the general formula (Ia) below:

(Ia)

[Structure showing two benzene rings with $R_2$ substituents, linked through CH and O-$R_7$ groups, with subscripts p and n]

in which each $R_2$ group, taken independently, is a sulfate group or a phosphate group, $R_7$ is a $(CH_2)_r$-Z group in which Z is a COOEt, COOH, CN or $NH_2$ group, r is a positive integer between 1 and 20, p is a positive integer between 1 and 10, and n is a positive integer between 2 and 10.

This invention still further relates to a macrocyclic adjuvant ligand grafted onto a functionalized support in which the ligand corresponds to the formula (Ib):

$$(Ib)$$

in which n is a positive integer between 4 and 8, each $R_2$ group, taken independently, is a sulfate group or a phosphate group, $R_8$ represents a $(CH_2)_t$—$(CO)_s$—$(NH_2)$ group or a $(CH_2)_t$—COOH group in which t is a positive integer between 0 and 6 and s is a positive integer between 0 and 6, and the support is a solid support functionalized by an NHS group or an $NH_2$ group and is a magnetic ball or a microplate.

This invention yet again relates to a diagnostic kit for diseases involving $PrP^{sc}$ including a macrocyclic adjuvant ligand of formula (I), free or bound to a support.

This invention further still relates to a kit for the immunological dosing of $PrP^{sc}$ including a macrocyclic adjuvant ligand of formula (I), free or bound to a support.

BRIEF DESCRIPTION OF THE DRAWINGS

FIG. 3 shows images in scanning probe microscopy (SPM) in non-contact mode for dried films of the recombinant protein prion (recPrP) alone (A), of recPrP in the presence of ALM1 (B) and of AML1 alone (C).

FIG. 4 shows images in scanning probe microscopy (SPM) in non-contact mode for dried films of recPrP in the presence of AML in different proportions: 1/1000 AML1/recPrP, 1/100 AML1/recPrP, 1/10 AML1/recPrP.

DETAILED DESCRIPTION

Figure 1:
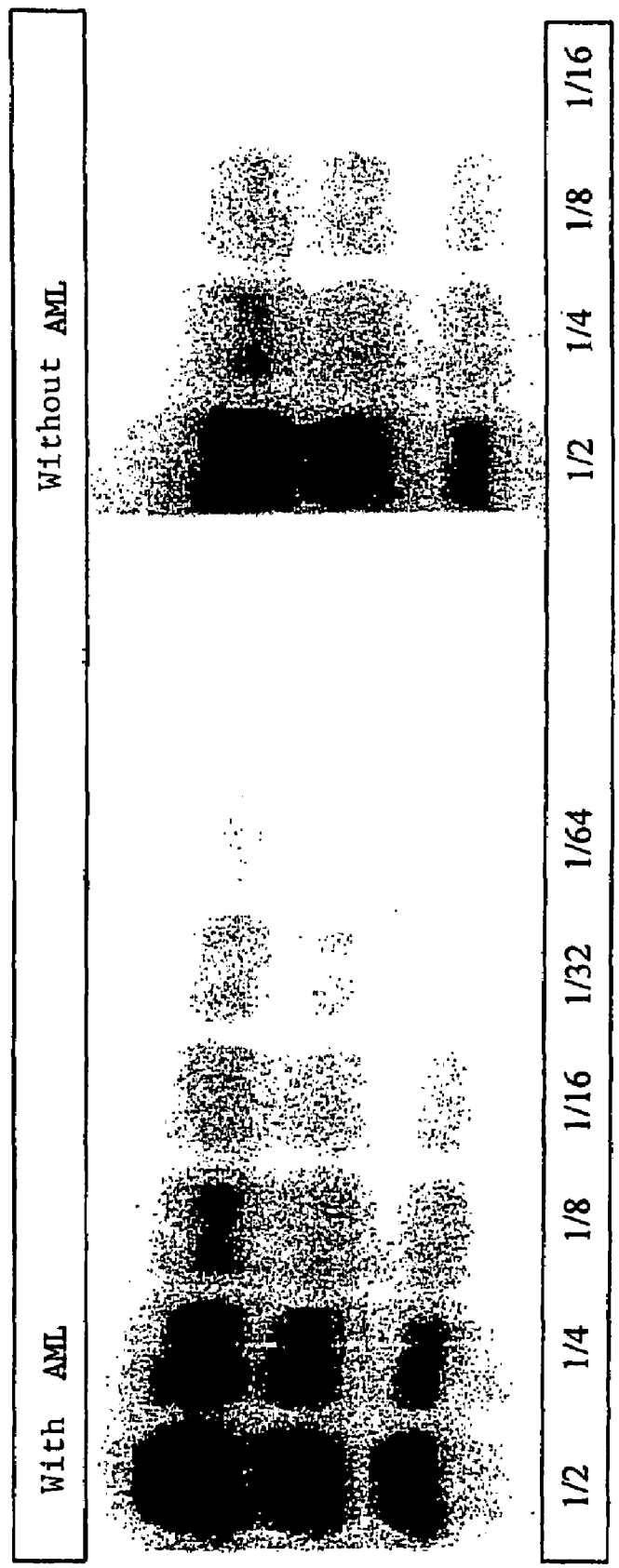
FIG. 1 is a comparative example of the detection by immunoblotting of $PrP^{sc}$ on the one hand in a sample placed in the presence of a specific macrocyclic adjuvant ligand (AML1) whose preparation is described below and, on the other hand, in a sample not placed in the presence of AML1.

This invention concerns a process permitting detecting the protein PrP and especially $PrP^{sc}$ in dilutions in which it can not be detected with the methods currently used, which detection has had a 100% reliability in 119 samples that we tested. The process in accordance with the invention advantageously permits the detection of $PrP^{sc}$ to be multiplied by a factor of 4.

More precisely, this invention concerns a process for detecting PrP and, in particular, $PrP^{sc}$, characterized in that: a macrocyclic adjuvant ligand (AML) that is free or linked to a support is added to a biological sample capable of containing PrP, the resulting suspension is then reacted with an anti-PrP antibody, and the presence of PrP is then detected.

The connection of the macrocyclic ligand to the support can be realized in a known manner such as by adsorption or covalent bonding, covalent bonding, otherwise called grafting, being preferred.

When the attempt is made to detect $PrP^{sc}$, the method can also comprise the supplementary step of treating the sample with proteinase K before or after contact with the AML.

The presence of PrP can be realized by detecting the antibody reaction anti-PrP/PrP, which can be done by any means known in the art, and especially by a sandwich method such as ELISA, immunoblotting, immuno micro-cantilever detection, mass spectrometry or by optical and spectroscopic analyses. Identification of the AML-PrP complex is made by profilometric scanning techniques such as scanning reflectance microscopy, near-field scanning microscopy or confocal scanning microscopy.

The biological sample may come from an animal, including humans. The sample preferably comes from the brain, tissues of the central nervous system or organs, in particular, the spleen or intestine. The sample may be a biological fluid, especially cerebrospinal fluid or serum.

The term "macrocyclic ligand" denotes a compound that is capable of bonding to PrP and, in particular, to $PrP^{sc}$ and constituted of a succession of cycles forming a macrocycle. Macrocyclic ligands are known. It is possible to cite by way of non-limiting example cyclophanes, metacyclophanes, cyclodextrins, cyclo(chromotropic tetra-acids), spherands and cyclo[n]veratrylenes.

The macrocyclic adjuvant ligand is advantageously capable of bonding to sites that are contiguous or close in space, sites for bonding with an antibody and has the effect of increaseing the antibody-$PrP^{sc}$ bond.

The macrocyclic adjuvant is advantageously selected from the family of metacyclophanes. Among the metacyclophanes, the para-sulfonato-calix-arenes functionalized on the phenolic face are particularly advantageous. These compounds can be obtained in accordance with the methodology described in Da Silva et al., J. Supramol. Chem. 1, (2001), pp. 135–138, the subject matter of which is hereby incorporated by reference.

The macrocyclic adjuvant ligand advantageously corresponds to the general formula (I) below:

(I)

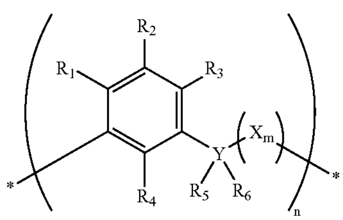

in which $R_1$ represents a hydrogen atom, a hydroxyl group, an OR group or an OCOR group with R as defined below, $R_2$ represents a hydrogen atom, a group R, COR, Pol, $CH_2Pol$ in which Pol represents a phosphate, sulfate, amine, ammonium, carboxylic acid group and R is as defined below, $R_3$ represents a hydrogen atom, a hydroxyl group, an OR group or an OCOR group in which R is as defined below, $R_4$ represents a hydrogen atom, a hydroxyl group, an OR group, an $OCH_2R$ group or an OCOR group in which R is as defined below, Y is an atom of carbon, nitrogen or an atom of sulfur, $R_5$ and $R_6$ are, each independently, absent or represent a hydrogen atom, a $CH_2$ group or R as defined below, or $R_5$ and $R_6$ together represent an atom of oxygen or of sulfur, X represents a $CH_2$ group or an atom of oxygen or of sulfur, m represents a positive integer equal to 0 or 1, R represents a hydrogen atom or a hydrocarbon chain, saturated or unsaturated, branched or unbranched, cyclic or non-cyclic, substituted or not substituted by a halogen group and carrying polar or non-polar functions, n is a positive integer between 3 and 15, and $R_1$ to $R_5$, R, X, Y and m can be different.

Thus, the compound of formula I is present in the form of a succession of n building blocks, characterized by the presence of a benzene ring, and in which the substituents of the ring can vary from one building block to the other within the limit of their above definitions.

The macrocyclic ligands can be prepared according to known techniques described, e.g., in "Comprehensive Supramolecular Chemistry," Pergamon, Oxford, 1996, the subject matter of which is hereby incorporated by reference.

The hydrocarbon chains, saturated or unsaturated, branched or unbranched, cyclic or non-cyclic, substituted or non-substituted by a halogen group and carrying polar or non-polar functions are well-known. Representative examples include alkyls, alkenes, aryls, and saturated cycles such as cyclohexane. An example of a non-polar group is $CF_3$ and examples of polar groups are the substitutents Pol as defined above.

The macrocyclic adjuvant ligand may correspond to general formula I above and more precisely to general formula Ia below:

(Ia)

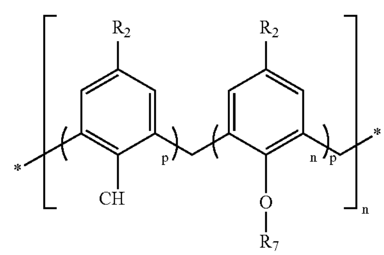

in which each $R_2$ group, taken independently, is a sulfate group or a phosphate group, $R_7$ is a $(CH_2)_r$-Z group in which Z is a COOEt, COOH, CN or $NH_2$ group, r is a positive integer between 1 and 20, p is a positive integer between 1 and 10, and n is a positive integer between 2 and 10.

The macrocyclic adjuvant ligand may be p-sulfonato-calix-[4]-arene, p-sulfonato-calix-[6]-arene, p-sulfonato-calix-[8]-arene or one of their derivatives.

The macrocyclic adjuvant ligand may also correspond to general formula I above and more precisely to general formula Ib below:

(Ib)

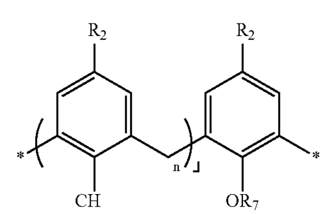

in which
n is a positive integer between 4 and 8,
each $R_2$ group, taken independently, is a sulfate group or a phosphate group, and
$R_8$ represents a $(CH_2)_t$—$(CO)_s$—$(NH_2)$ group or a $(CH_2)_t$—COOH group in which t is a positive integer between 0 and 6 and s is a positive integer between 0 and 6.

The calyx-arene of formula Ib is advantageously such that each of the two $R_2$ groups is a sulfate group, n is 4, 6 or 8 and $R_8$ is a hydrogen atom, a $CH_2COOH$, a $CH_2CONH_2$ group or a $CH_2CH_2NH_2$ group.

The calyx-arene of formula Ib is preferably such that each of the two $R_2$ groups is a sulfate group, n is a positive integer equal to 6 and $R_7$ is a $(CH_2)_2$—$NH_2$ group.

The ligand in accordance with the invention may be grafted onto a solid support. This support is functionalized by a function capable of forming a bond with a function carried by the ligand. The solid support may be functionalized by an NHS(N-hydroxysuccinimide) bond or an $NH_2$ function. This function can react with a function carried on the ligand. In that case, the calyx-arenes carrying a function capable of reacting to form a bond with the functional bond of the solid support, in particular the calyx-arenes carrying a $NH_2$ or COOH bond, are particularly preferred.

The invention also concerns a macrocyclic adjuvant ligand grafted onto a functionalized support in which the ligand corresponds to formula Ib as defined above in which n is a positive integer between 4 and 8 and the support is of the solid support type preferably functionalized by an NHS group or an $NH_2$ group and is preferably a magnetic ball or a microplate. Such a graft preserves the later interaction between the protein and the ligand as well as the stereochemical presentation of the epitope for detection by an anti-PrP antibody. The sites targeted by the graft on the support are different than those that serve for the interaction with the PrP.

The macrocyclic adjuvant ligand may be selected from the family of cyclodextrins and, in particular, of cyclodextrins corresponding to general formula II:

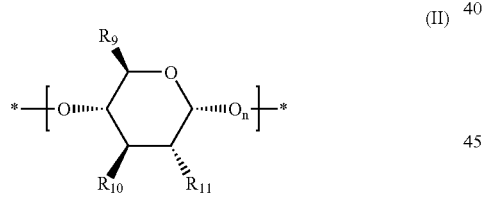

(II)

in which
$R_9$ represents a hydrogen atom or a $CH_2$, OH, OR, OCOR, COR, $CH_2Pol$, $OCH_2R$, SR, NR, Pol group and R is defined below,
$R_{10}$ and $R_{11}$ represent, each independently, a hydrogen atom or a $CH_2$, OH, OR, OCOR, COR, $CH_2Pol$, $OCH_2R$, Pol group and R is defined below,
Pol represents a phosphate, sulfate, amine, ammonium or carboxylic acid group,
R represents a hydrocarbon chain, saturated or unsaturated, branched or unbranched, cyclic or non-cyclic, substituted or non-substituted by a halogen group and carrying polar or non-polar functions,
n is a positive integer between 6 and 8, and
the substituents $R_9$ to $R_{11}$ can be different by nature in accordance with the building blocks. Thus, the compound of formula II is present in the form of a succession of n building blocks characterized by the presence of a cyclic group, and the substituents of this cyclic group can be variable from one building block to the other within the limit of their above definitions.

The macrocyclic adjuvant ligand may be selected from the family of chromotropic cyclo-tetra-acids and, in particular, the chromotropic cyclo-tetra-acids corresponding to general formula III:

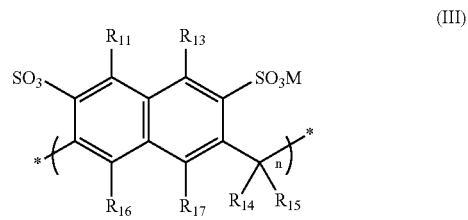

(III)

in which
$R_{12}$ and $R_{13}$ represent, each independently, a hydrogen atom or an R or Pol group as defined below,
$R_{14}$ and $R_{15}$ represent, each independently, a hydrogen atom a $CH_2$ group or an R group as defined below, or
$R_{14}$ and $R_{15}$ together represent an atom of oxygen or of sulfur,
$R_{16}$ and $R_{17}$ represent, each independently, a hydrogen atom or a hydroxyl group or an OR, $OCH_2R$, OCOR, SR, $SCH_2R$, SCOR group in which R is defined as below,
M represents a hydrogen atom or an atom selected from Na, K, Li, Cs, Rb, Mg and Ca,
Pol represents a phosphate, sulfate, amine, ammonium or carboxylic acid group,
R represents a hydrocarbon chain, saturated or unsaturated, branched or unbranched, cyclic or non-cyclic, substituted or non-substituted by a halogen group and carrying polar or non-polar functions,
n is a positive integer between 3 and 15, and
$R_{12}$ to $R_{17}$, M, Pol and R can be different by nature in accordance with the building blocks. Thus, the compound of formula III is present in the form of a succession of n building blocks characterized by the presence of a cyclic group, and the substituents of this cyclic group can be variable from one building block to the other within the limit of their above definitions.

The macrocyclic adjuvant ligand may also be selected from the family of cyclo [n] veratrylenes, corresponding to general formula IV:

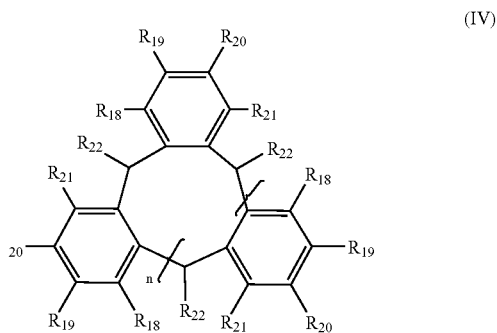

(IV)

in which $R_{18}$ represents a hydrogen atom or a $CH_2$, OH, OR, OCOR, COR, $CH_2Pol$, $OCH_2R$, SR, NR, Pol group and R is as defined below, $R_{19}$, $R_{20}$, $R_{21}$ and $R_{22}$ represent, each independently, a hydrogen atom or a $CH_2$, OH, OR, OCOR, COR, $CH_2Pol$, $OCH_2R$, Pol group and R is as defined below, Pol represents a phosphate, sulfate, amine, ammonium or carboxylic acid group, and R represents a hydrocarbon chain, saturated or unsaturated, branched or unbranched, cyclic or non-cyclic, substituted or non-substituted by a halogen group and carrying polar or non-polar functions, n is a positive integer between 1 and 10, and $R_{18}$ to $R_{22}$, R, Pol and R can be different by nature in accordance with the building blocks. Thus, the compound of formula IV is present in the form of a succession of n building blocks characterized by the presence of a cyclic group, and the substituents of this cyclic group can be variable from one building block to the other within the limit of their above definitions.

Other subject matter of the invention comprises use of a macrocyclic adjuvant ligand (AML) for detecting the $PrP^{sc}$ prion in a biological sample and, in particular, a ligand of formula I, Ia or Ib above, free or bound to a support.

The invention also has as subject matter a kit for diagnosing diseases of which $PrP^{sc}$ is responsible and of the type ESB, trembling of small ruminants, Creutzfeld-Jakob, comprising the use of the macrocyclic adjuvant ligand and, in particular, a ligand of formula I, Ia or Ib above, free or bound to a support.

The invention also has as subject matter a kit for immunological dosing of $PrP^{sc}$, comprising the use of a macrocyclic adjuvant ligand and, in particular, a ligand of formula I, Ia or Ib above, free or bound to a support.

Other advantages and features of the invention will appear from a reading of the following examples concerning the amplification of the detecting of $PrP^{sc}$ when the biological sample is placed in the presence of a free or grafted macrocyclic adjuvant ligand.

EXAMPLE 1

Preparation of Macrocyclic Adjuvant Ligands 1.1 Preparation of p-sulfonato-3,7-(2-carboxy-methyloxy)-calix-[6]-arene (Called AML 1)

This macrocyclic adjuvant ligand AML1 has the general formula V:

(V)

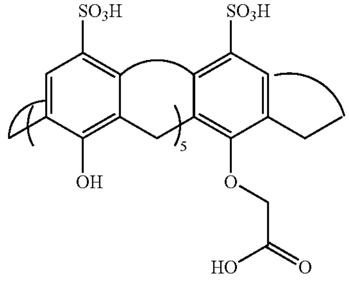

This ligand was synthesized as follows: A suspension of calyx[6]arene in acetonitrile in the presence of a base equivalent ($K_2CO_3$) was agitated on reflux. After 30 minutes, 0.5 equivalent of alkylating agent (ethyl bromoacetate) was added to the reaction mixture, that was maintained on reflux and under agitation 24 hours. After cooling of the suspension the solvent was evaporated under reduced pressure and the resulting solid was dissolved in 200 ml $CH_2Cl_2$ and washed twice with a solution of hydrochloric acid (1M) and once with demineralized water. After having dried on magnesium sulfate ($MgSO_4$) the organic solvent was evaporated under reduced pressure and permits the obtention of a white powder. This powder was purified on a silica chromatography column (eluent: $CH_2Cl_2$: hexane; 4:1). The purified product was analyzed in RMN of $^1H$, $^{13}C$ and in mass spectrometry electrospray. The saponification of the carboxylic ester was performed by potassium hydroxide in solution in a mixture of water:ethanol (30:70) under agitation at ambient temperature 24 hours. The precipitate formed was filtered, then washed with 50 ml hydrochloric acid (1M) and 50 ml water, then purified on a silica chromatography column (eluent chloroform:methanol:acetic acid; 95:5:0.1%) and permits the obtention, after evaporation of the solvent, of a white and crystalline solid. This product is analyzed in RMN of $^1H$, $^{13}C$ and in mass spectrometry electrospray. The sulfonation was performed by a treatment with sulfuric acid at 50° for 24 hours. The product was precipitated with ether and permits the obtention of AML1 in the form of a white crystalline powder.

1.2 Preparation of p-sulfonato-3,7-(2-aminoethyloxy)-calix-[6]-arene (Called C6S)

This macrocyclic adjuvant ligand C6S has the general formula VI:

(VI)

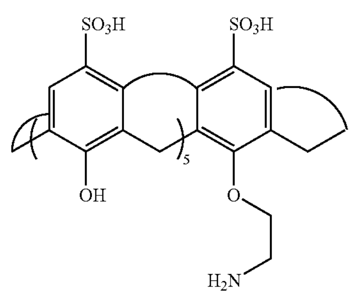

This ligand was prepared in accordance with the method described in Eric Da Silva and Anthony W. Coleman, Synthesis and Complexation Properties towards Amino Acids of Mono-Substituted p-sulfonato-calix-[n]-arene, Tetrahedron 59 (2003), pp. 7357–7364, the subject matter of which is hereby incorporated herein.

1.3 Grafting of Ligand C6S on Plates and on Balls

This ligand was coupled with a solid support (ball or plate) carrying an active surface.

Grafting on Plate:

The plates “NHS-activated plates” with 96 sinks came from the Covalab company (Lyon, France). 100 μl of a solution of ligand are dissolved at different concentrations in phosphate buffer 50 mM, pH 8.2. The sinks were washed 3 times (3×200 μl) MilliQ water after two hours of incubation at 37° C. The plates were dried at ambient temperature before being used.

Grafting Scheme:

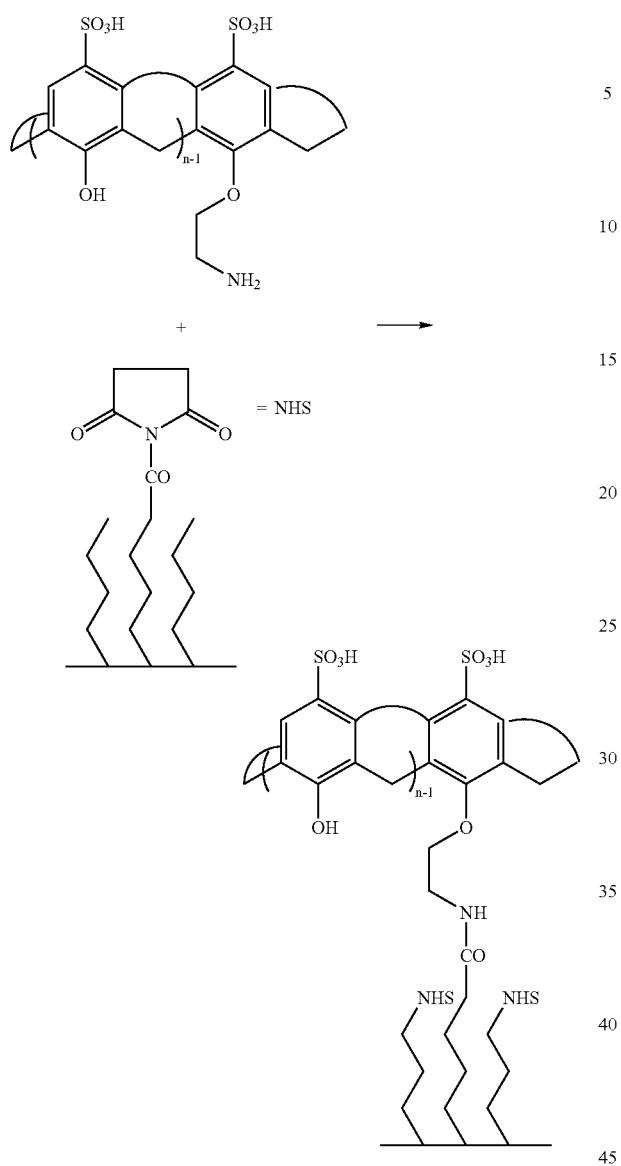

Scheme of Grafting C6S on the Balls:

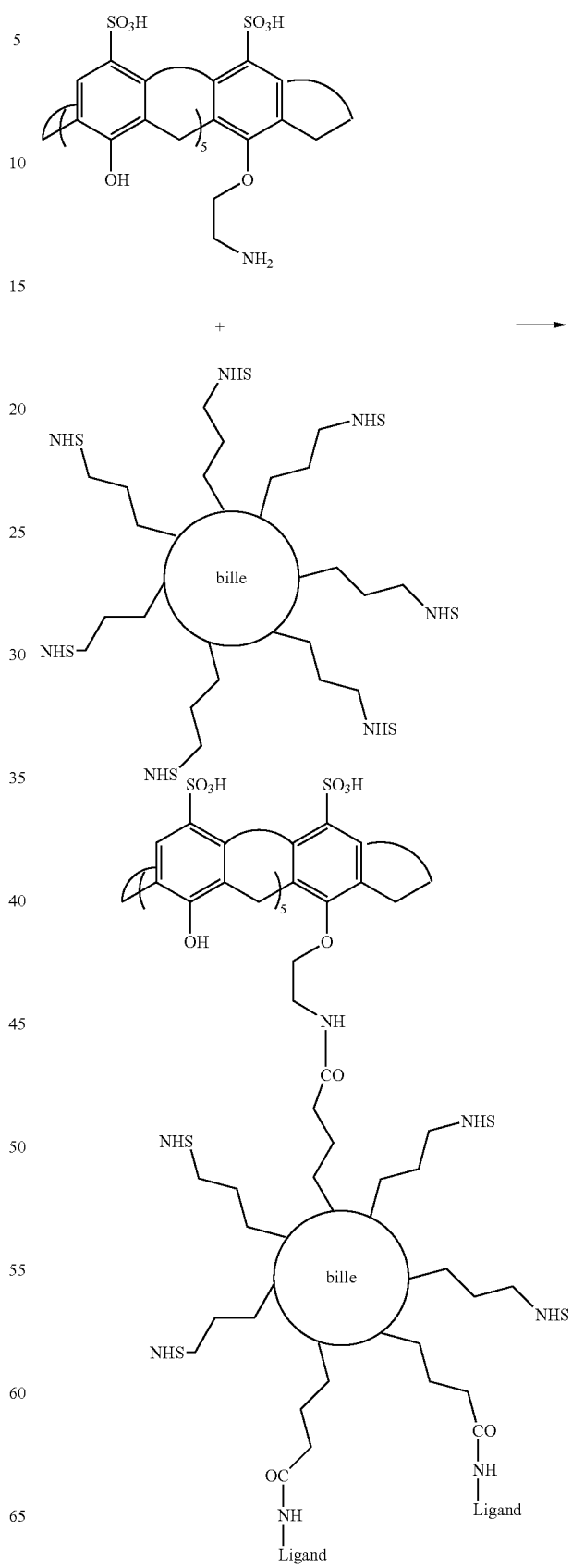

Several plates were made at different concentrations in ligand C6S. These plates are defined as "plates C6S" in the entire text.

Grafting on Balls:

4 ml of a solution of activated ball NHS ($2 \times 10^9$ balls/ml; Dynabeads® M270amine, Dynals company, Norway) were aliquoted in tubes of 1 ml. The balls were centrifuged and precipitated by magnetization. The supernatant was removed and the balls washed 3 times with 1 ml water. The ball bottom was reworked with different volumes of solution of calixarene in a phosphate buffer 50 mM, pH 8.2. 600 ml, 120 ml, 60 ml and 12 ml of a ligand solution at 50 mg/ml (phosphate buffer 50 mM, pH 8.2) are added. The balls were agitated 24 hours at ambient temperature. The balls were washed 3 times with MilliQ water 18 Ω to eliminate the ligand that did not react. The balls were preserved in 1 ml water to reconstitute the initial concentration of $2 \times 10^9$/ml. The ball solution was then ready for use. These balls are defined as "balls C6S" in the entire text.

1.4 Grafting of AML1 onto a Modified Mineral Surface 1 ml 3-aminopropyltrimethoxysilane (ABCR company) were placed in solution in a solution of 50 ml (95% ethanol and 5% $H_2O$) for 5 min. The silicon plate was immersed into this solution for 4 min under agitation. The silicon plate was rinsed with ethanol, then the plate set to dry at 130° C. for 15 min. 10 ml AML1 in solution 0.1 M in DMSO was coupled on a modified silicon plate using a coupling agent (DCC/HOBT). The sample was dried 12 hours at 23° C.

Coupling Scheme:

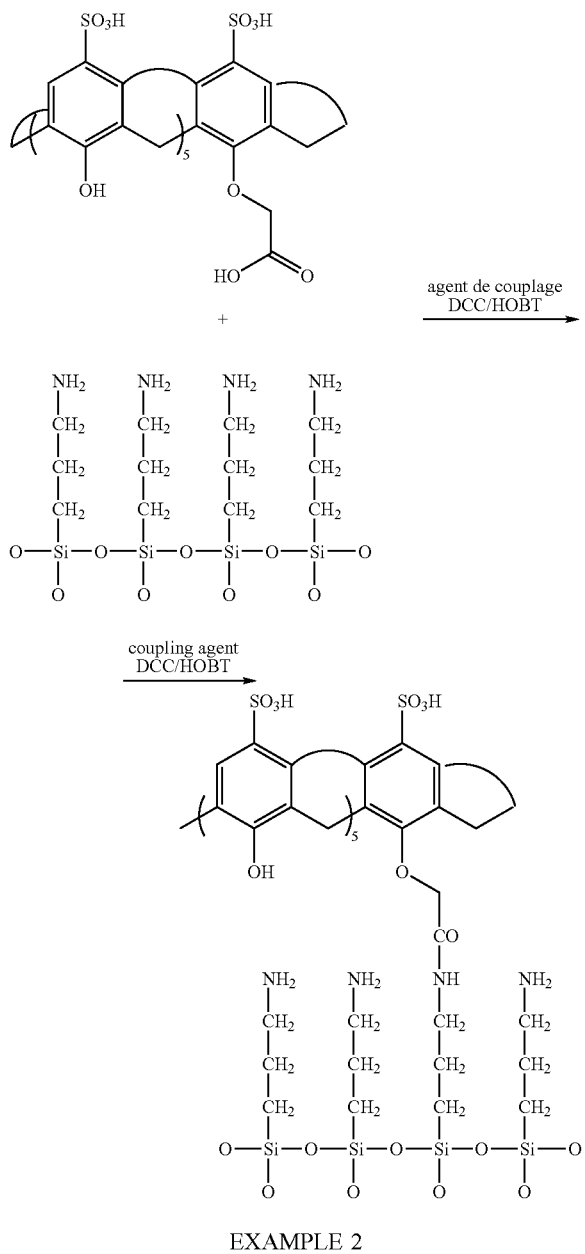

EXAMPLE 2

Detection of PrP Using AML1 not Coupled to a Solid Support

2.1 Preparation of Samples

The samples that were used for the examples of FIGS. 1 and 2 were prepared as follows:

Sample without AML: 0.5 g brain tissue was crushed in 4.5 ml 5% glucose solution to obtain a suspension with 10% weight/volume. 1 µg proteinase K (Boehringer) in 10 µl was added per 100 µl brain homogenate at 10% in glucose at 5% (equivalent to 10 mg of brain). The solution was placed under vortex and incubated at 37° C. for another hour. After the addition of 100 µl denaturing Laemmli buffer, the mixture was heated 5 minutes at 100° C., centrifuged at 12000 G for 5 nm, and the supernatants recovered to make them migrate on SDS PAGE.

Sample with AML: 0.5 g brain tissue was crushed in 4.5 ml 5% glucose solution to obtain a suspension with 10% weight/volume. 1.5 µg proteinase K (Boehringer) in 10 µl was added per 100 µl brain homogenate at 10% in glucose at 5% (equivalent to 10 mg of brain). The solution was placed under vortex and incubated at 37° C. for another hour. After the addition of 100 µl denaturing Laemmli buffer, the mixture was heated 5 minutes at 100° C., centrifuged at 12000 G for 5 nm, and the supernatants recovered to make them migrate on SDS PAGE.

2.2 Process for Detection by Immunoblotting

After migration on a one-dimensional electrophoretic gel of 15% polyacrylic amide in the presence of sodium dodecyl sulfate (SDS PAGE) as described by Laemmli, Nature 227 (1970), pp. 680–685, the proteins were transferred by electrophoresis onto nitrocellulose membranes and immunoblotted at ambient temperature 60 minutes with a monoclonal antibody recognizing a specific epitope constituted of amino acids 126–160. The secondary antibody (1/5000) was a goat antibody directed against the heavy and light chains of the mice immunoglobulins conjugated on horseradish peroxidase (IgG H+L).

The blots were then washed and the signals detected by chemiluminescence either with an ECL kit (Amersham) on films (Biomex light, Kodak) or with a super Signal Ultra (Pierce) and visualization on Fluor S. Multimager (BioRad).

Figure 2:
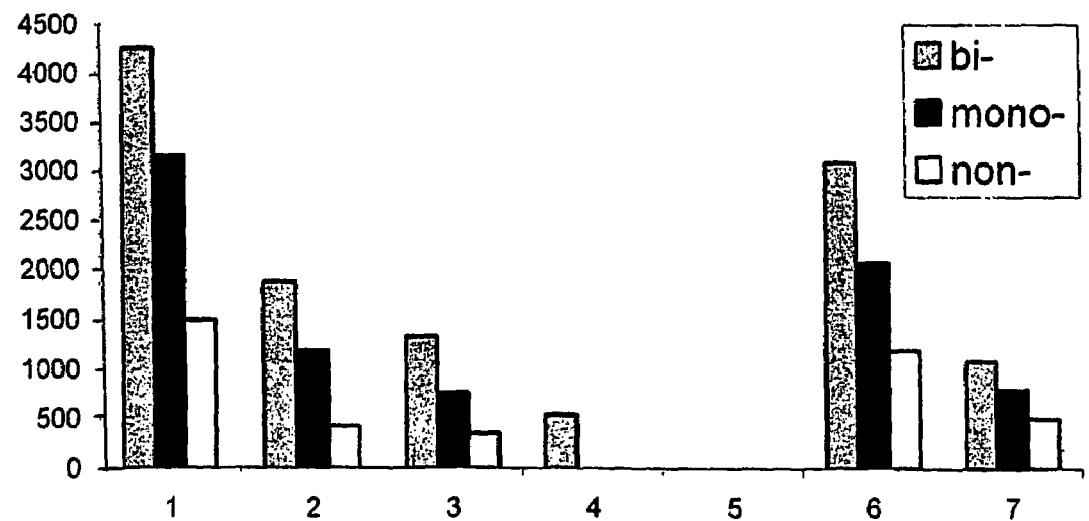
FIG. 2 shows optical density curves of the detection of $PrP^{sc}$ on the one hand in a sample placed in the presence of AML1 and on the other hand in a sample not placed in the presence of AML1.

FIG. 1 is a comparative example that shows that detection of the prion is increased at least four times when the process of the invention is used over the detection of the same protein in the absence of AML1. In the absence of AML1, no $PrP^{sc}$ is detected for dilutions greater than $\frac{1}{8}^{th}$. In the presence of AML, detection of $PrP^{sc}$ in the same sample is possible up to a dilution of $\frac{1}{32}^{nd}$. The results of FIG. 2 show the detection.

2.3 Microscopy Results

The samples used for the experiments in probe scanning microscopy reported in FIGS. 3 and 4 were prepared as follows:

Samples containing only macrocyclic adjuvant ligand: The samples containing macrocyclic adjuvant ligand (50 mM) were prepared by depositing 10 µl AML solution and 10 µl water on freshly split mica and are dried 24 hours at 37° C.

Samples containing only recombinant PrP protein (recPrP): the samples containing recPrP were prepared by depositing 10 µl of solution of 1/10 (v/v) AML1/recPrP, 1/100 (v/v) AML1/recPrP and 1/1000 (v/v) AML1/recPrP and 10 µl water on freshly cut mica and dried 24 hours at 37° C.

Samples containing macrocyclic adjuvant ligand and recPrP at the same time: 1) Samples containing macrocyclic adjuvant ligand and recPrP at the same time were prepared by depositing 1 µl AML solution and 1000 µl recPrP on freshly split mica and dried for 24 hours at 37° C.; 2) Samples containing macrocyclic adjuvant ligand and recPrP at the same time were prepared by depositing 1 µl AML solution and 100 µl recPrP on freshly cut mica and dried for 24 hours at 37° C.; 3) Samples containing macrocyclic adjuvant ligand and recPrP at the same time were prepared by depositing 1 µl AML solution and 10 µl recPrP on freshly cut mica and dried for 24 hours at 37° C.

An imaging analysis is performed with a Thermomicroscope Explorer AFM equipped with a 100 µm tripod scanner in non-contact mode using elevated resonance frequencies ($F_0$=320 kHz) of pyramidal cantilever with silicone probes at a scanning frequency of 1 Hz. The processing of the images is performed with SPMlab 5.1 software and presented non-filtered.

It follows from FIGS. 3 and 4 that only the films of recPrP show a characteristic structure in circular aggregates. In the presence of AML, the structures observed for recPrP are modified sequentially, are an increasing function of the quantity of AML and show building blocks that are rounded and possibly orthogonal crystallite. The images of only macrocyclic adjuvant ligand (AML1) show structures that are similar, but smaller than the building blocks of the recPrP—AML films.

Other experiments were carried out by atomic force microscopy.

A subsequent analysis by surface analysis of the rugosity is presented in Table I. The use of these rugosity measurements can be extended to techniques of profilometric analyses.

TABLE I

|  | AML only | AML/recPrP 1/1000 | AML/recPrP 1/100 | AML/recPrP 1/10 | recPrP only |
|---|---|---|---|---|---|
| Ra (nm) | 48 | 69.6 | 123.9 | 134.4 | 1.11 |
| RMS (nm) | 58.7 | 82.8 | 149 | 163.1 | 1.95 |
| Average height | 217.7 | 233.3 | 408.7 | 469.8 | 5.4 |
| Maximum height value | 448.9 | 484.3 | 894.66 | 1056.9 | 43.17 |

$$R_a = \frac{1}{N}\sum_{i=1}^{N}|z_i - \bar{z}|$$

(Formula A)

$$RMS = \sqrt{\frac{1}{N}\sum_{i=1}^{N}(z_i - z)^2}$$

(Formula B)

$$\text{Avg Height} = \frac{1}{N}\sum_{i=1}^{N}z_i$$

(Formula C)

The calculated rugosity values are obtained with the Thermomicroscope SPML 5.01 software. The average rugosity Ra is defined as the arithmetic mean of the deviations in height (Formula A), the root mean square rugosity RMS is defined as the square root of the average value of the squares of the distances of the points at an average image value (Formula B) and the average height of the sample (Formula C).

EXAMPLE 3

Detection of Recombinant PrP Using the C6S Graft on a Solid Support

3.1 Detection of Bovine Recombinant PrP on Plates a) Protocol

The protocol used in this experiment was from a classic ELISA.

According to Example 1, grafting of activated amine plates (NHS) was performed for 6 hours with a range of sulfonated calix-6-arenes (C6S) diluted in a solution of PBS 50 mM (saline phosphate buffer). The plates were then rinsed with distilled water before being saturated with a solution of PBST (PBS Tween) (0.05% milk 5%) for 1 hour at ambient temperature. After rinsing, a solution of recombinant bovine protein prion (PrP) diluted to a concentration of 0.25 µg/ml was deposited in PBST 0.05%. It was incubated one hour at ambient temperature. The plate was rinsed again three times. It was then incubated with a solution of anti-PrP antibodies marked with peroxidase diluted at 0.5 µg/ml in PBST 0.05% for one hour at ambient temperature. The antibody used recognizes the region defined by the amino acids 145–154 of human PrP and the homologous regions of animal PrP (AC23). Finally, after a new rinsing cycle the developer, a solution of OPD (ortho-phenylene diamine), was added and incubated 10 minutes at ambient temperature away from light. The reaction was stopped with the aid of a solution of $H_2SO_4$. The signal obtained was read with the aid of a spectrophotometer at 495 nm.

b) Results

Figure 5:
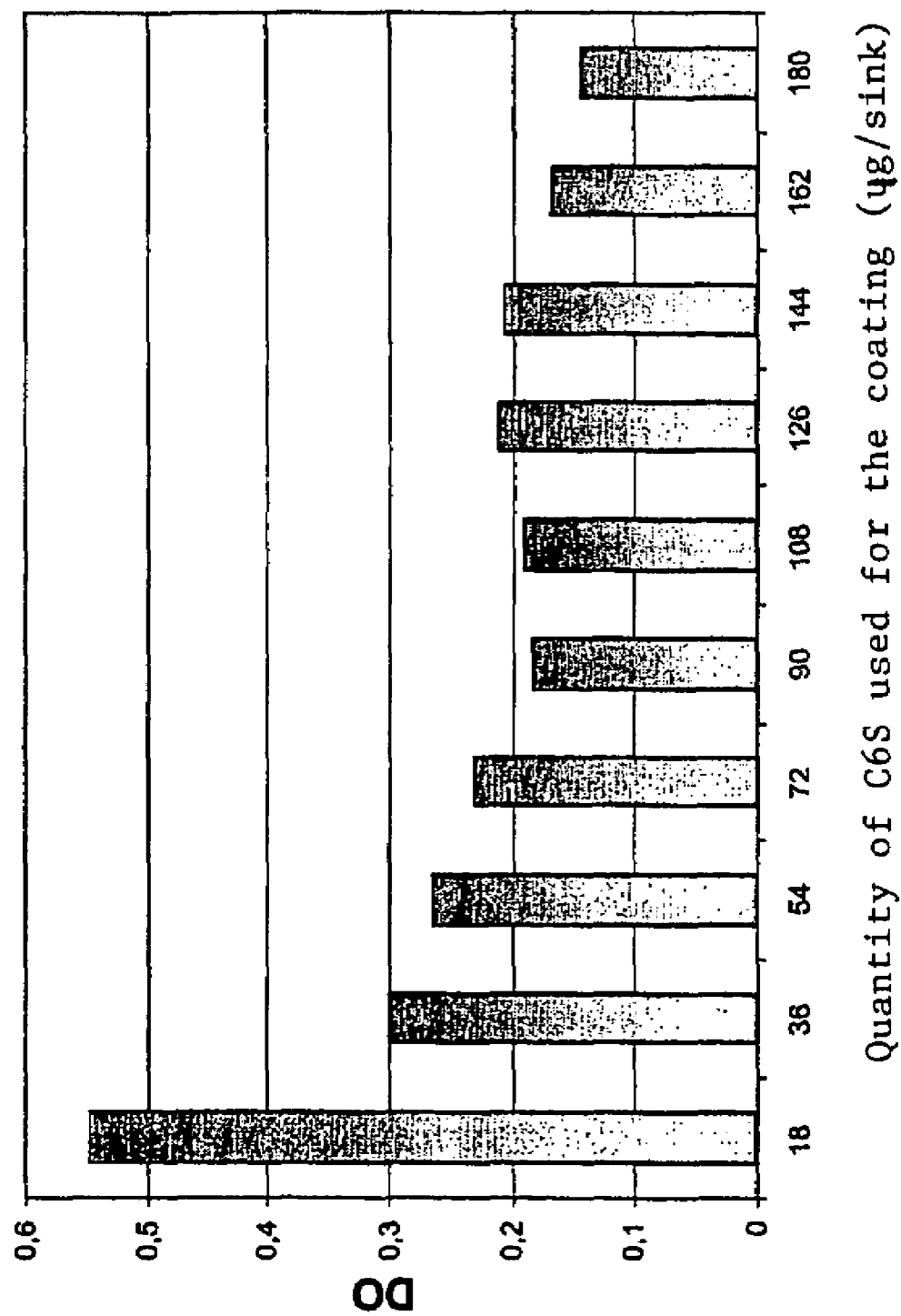
FIG. 5 shows a graphic representation giving the values of optical density (DO) obtained as a function of the concentration of calyx-arene C6S grafted onto an activated amine plate (NHS) after incubation of a solution of recombinant bovine PrP and disclosure by the anti-PrP AC23 antibody marked with peroxidase.

The results are indicated in FIG. 5, that shows that the optical density (DO) measured in the ordinate reflects the quantity of PrP captured by the C6C'es and remaining caught after washings. The signal obtained for the different graftings shows that the recombinant bovine PrP is captured well by the C6S'es. The bovine recombinant PrP fixes to the C6S'es grafted on the NHS plates.

3.2 Detection of Recombinant Human PrP on Balls a) Experiment Conditions

According to Example 1, the NHS balls were first placed in contact with a solution of C6S diluted in distilled water for grafting the C6S onto the balls. After this period, the balls were washed with distilled water then with PBST 0.05%. A solution of recombinant human PrP dosed at 0.25 µg/ml in PBST 0.05% is prepared in parallel. Then, a range of C6S balls was realized by adding: 0, 0.1, 1, 5 and 10 µl of the ball solution per 100 µl of the PrP solution. The incubation lasts 1 hour at 37° C., then the balls were separated from the supernatant by magnetization. The PrP fixed on the balls was dosed directly with the aid of an antibody marked in accordance with a sandwich method close to the ELISA method.

The developer antibody marked with peroxidase is incubated one hour at 37° after rinsings of the balls by a solution of PBST 0.05%. The balls are separated from the supernatant by magnetization before being washed again, then revealed by a solution of OPD incubated 10 minutes. The reaction was stopped with the aid of a solution of $H_2SO_4$. The developer antibody used was 8D11G12 (bioMerieux, France).

The reading of the signal obtained was made with the aid of a 495 nm spectrophotometer.

b) Results

Figure 6:
FIG. 6 shows a graphic representation giving the values of optical density (DO) obtained as a function of the concentration of calyx-arene C6S grafted on an activated amine ball (NHS) after incubation of a solution of human recombinant PrP dosed at 0.25 µg/ml by direct disclosure with the anti-PrP 8D11G12 antibody marked with peroxidase.

The results of the developments on ball are indicated in FIG. 6 and show that the C6S'es are correctly grafted without loss of function on the NHS supports, but especially retain their property of capturing the recombinant PrP of different species and even amplify the signal obtained with the specific antibodies of this protein in a reproducible manner.

EXAMPLE 4

Detection of Physiological PrP Using C6S Grafted on a Solid Support 4.1 Human Serum on Balls a) Protocol According to Example 1, the NHS balls were first placed in contact with a dilute solution of C6S in distilled water for grafting. After this period, the balls were washed with distilled water then with 0.05% PBST.

A serum range was prepared by dilution in PBS. A solution of human recombinant PrP dosed at 0.25 µg/ml into PBS was prepared in parallel as well as a solution of 0.05% PBST milk 5% that served as positive and negative controls.

The balls were added at the rate of 5 µl of a solution of $2.10^{e}9$ balls/ml per 250 µl of sample. The incubation took 1 hour at 37° C. under agitation. The balls were then separated from the supernatant by magnetization. The PrP fixed on the balls was dosed directly with the aid of a marked antibody.

The developer on the balls used a protocol close to ELISA. The developer antibody marked with peroxidase was incubated for one hour at 37° C. and under gentle agitation after rinsing of the balls by a solution of 0.05% PBST. The balls were separated from the supernatant by magnetization before being rewashed then revealed by a solution of OPD incubated for 10 minutes. The reaction was stopped with the aid of a solution of $H_2SO_4$. The developer antibody used was 8D11G12.

The reading of the signal obtained was made with the aid of a 495 nm spectrophotometer.

b) Results

Figure 7:
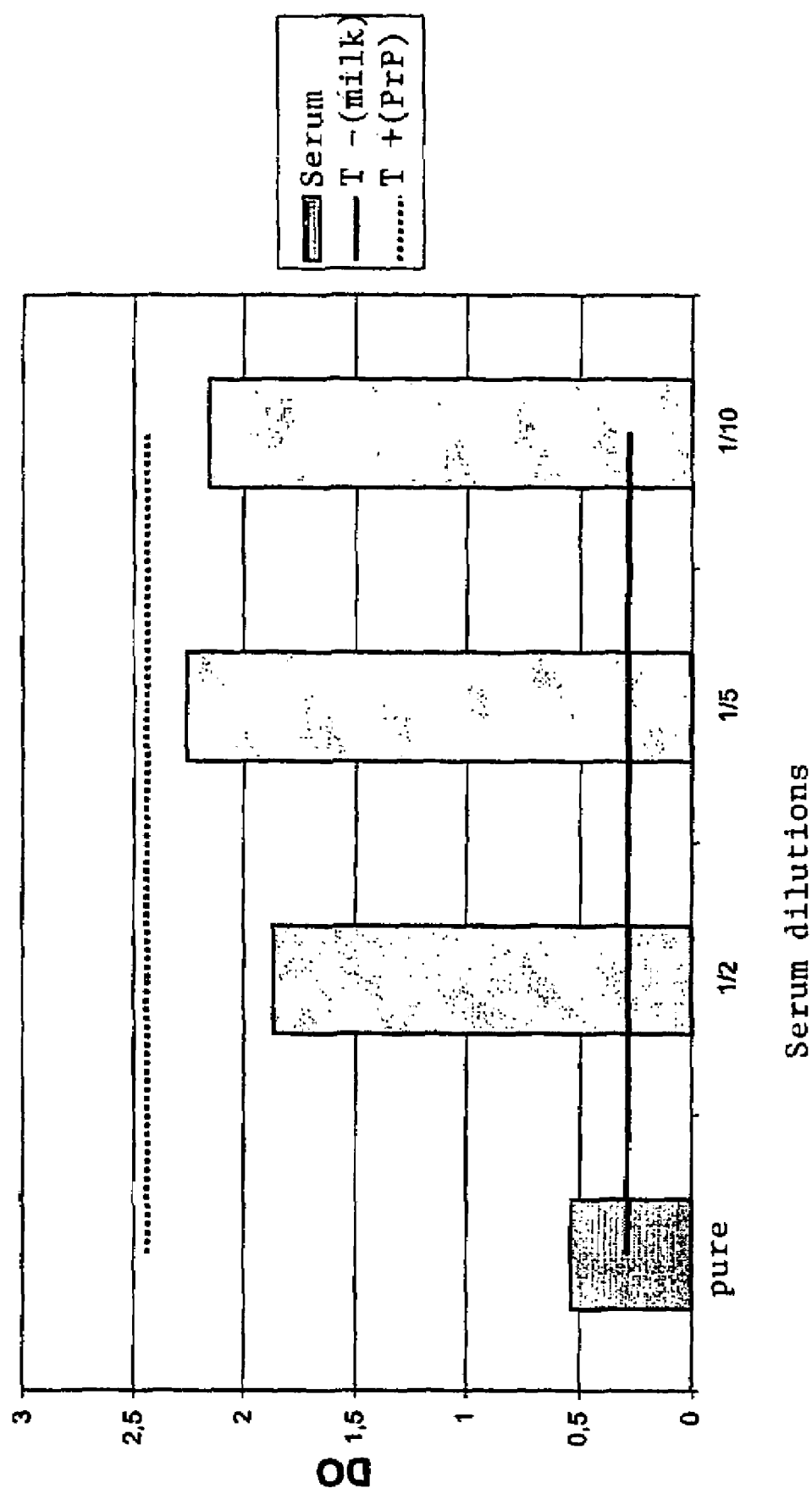
FIG. 7 shows a graphic representation giving the values of optical density (DO) obtained after incubation with a dilution range of human serum in PBST 0.05% placed in contact with calyx-arene C6S grafted on an activated amine ball (NHS) by direct disclosure with the anti-PrP 8D11G12 antibody marked with peroxidase.

The results are indicated in FIG. 7, that shows that:

The negative control in the milk permits evaluation of the background noise, whereas the positive control in a solution of 0.25 µg/ml PrP permits a verification that the experiment functioned and is interpretable.

The C6S'es grafted on the NHS balls captured the physiological PrP present in human serum. Moreover, the capture was better when the dilution of the serum was augmented with a saturation plate achieved for the dilutions at $1/5^{th}$ and $1/10^{th}$.

c) Conclusion

Surprisingly, the C6S'es grafted on NHS balls captured the physiological PrP present in human serum. The dilutions of the serum permit the signal obtained on the balls to be augmented.

4.2 Liquid Human Cerebrospinal Fluid (LCR) on Plates a) Experiment Conditions

The samples of LCR were first divided in tubes of equivalent volumes. Two dilution points: pure and ½ are established for each sample. Then, they were subjected to three types of heat treatment: 30 minutes at 56° C., 15 minutes at 75° C. or 5 minutes at 95° C. A control without heating was performed in parallel for the pure samples.

According to Example 1, in parallel, the NHS plates were placed in contact for 6 hours with a solution of C6S diluted in a solution of PBS 50 mM for grafting.

The plates were then rinsed with distilled water then with 0.05% PBST.

The samples were then deposited and incubated one night at 2–8° C. The plate was then rinsed six times. It was then incubated with a solution of anti-PrP antibody marked with biotin diluted at 0.5 µg/ml in 0.05% PBST for one hour at ambient temperature. The antibody used is AC23.

After a new rinsing cycle, a solution of streptavidine-PAL (alkaline phosphatase) was added and incubated for 20 minutes at ambient temperature. The plate was rinsed a last time and the developer solution of PNPP deposited and incubated for 30 minutes at 37° C. The reaction was stopped with the aid of a solution of NaOH 0.4N.

The reading of the signal obtained was made with the aid of a 495 nm spectrophotometer against a 490 nm filter.

b) Results

Figure 8:
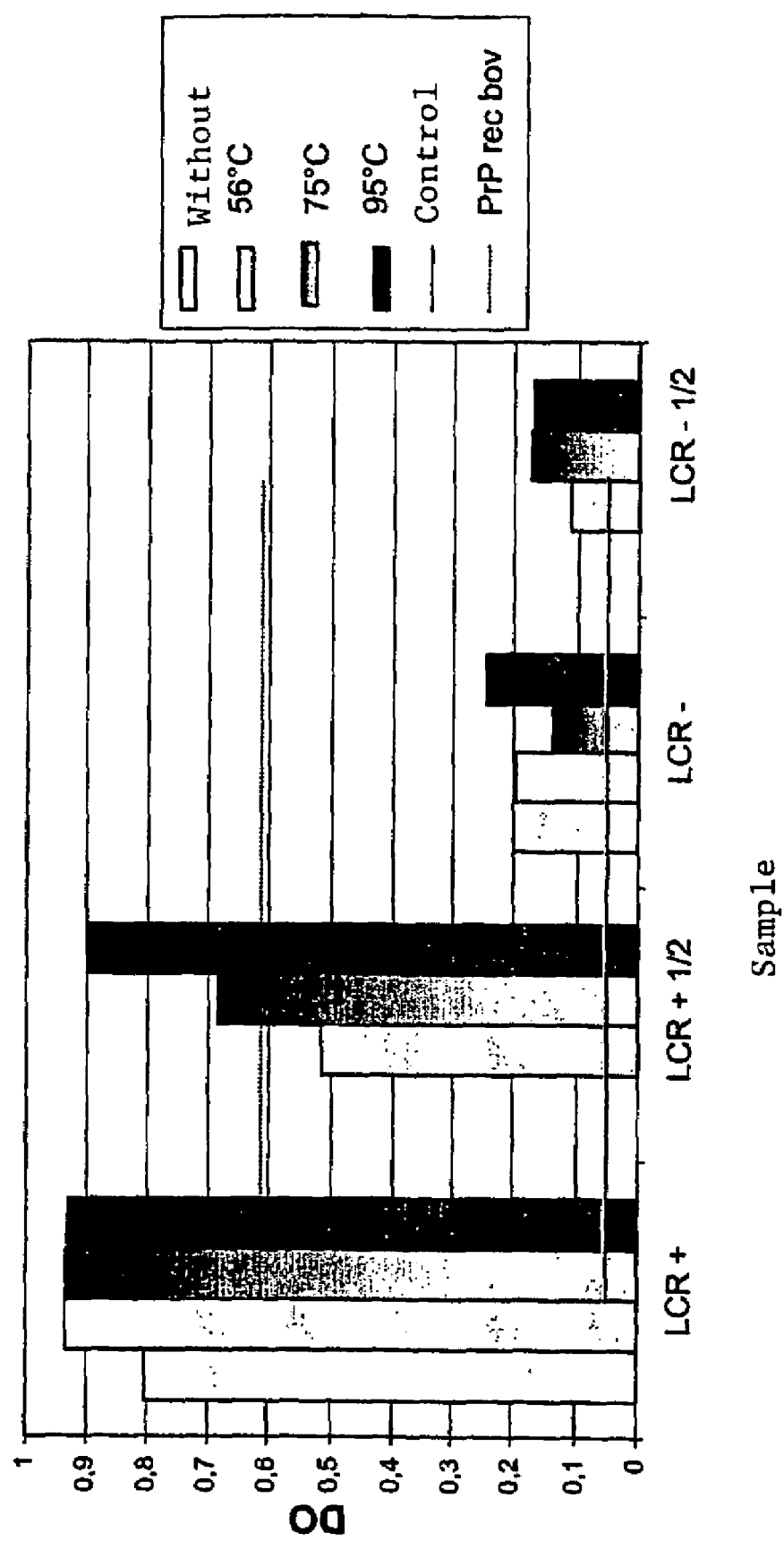
FIG. 8 shows a graphic representation giving the values of optical density (DO) obtained after placing calyx-arene C6S grafted on an activated amine plate (NHS) in contact with samples of positive (LCR+) and negative (LCR−) human cerebrospinal fluid for MJC as a function of the heating by disclosure with the anti-PrP AC23 antibody marked with alkaline phosphatase.

The results are indicated in FIG. 8, that shows that the physiological PrP can be dosed in the LCR.

EXAMPLE 5

Detection of PrP$^{sc}$ in the Brain Using C6S Grafted onto a Solid Support 5.1 Detection on Plate a) Experiment Conditions The first stage consists of obtaining PrP$^{sc}$ purified by extraction from the brains of patients affected or not affected by Creutzfeldt-Jakob disease (MJC). A sample of 260 mg of each brain was taken, then crushed to obtain a 10% homogenate in 5% glucose. The ground matter was then filtered with the aid of a needle. A digestion stage by proteinase K followed. It was used at a concentration of 20 µg per 100 mg of tissue at 37° C. for one hour. Then, 650 µl of a 30% Sarkosyl solution was added. A cushion of 400 µL saccharose was deposited in parallel on the bottom of a tube for ultracentrifugation. The sample was then deposited on this cushion. The tubes were completed before being welded, then ultracentrifuged for 2 hours at 20° C. at 100,000 rpm. The supernatants were eliminated and the tube walls roughly dried with absorbent paper. The bottoms were then put in tris maleate. The samples were then heated for five minutes at 95° then centrifuged 15 minutes at 12,000 rpm at 20° C. The samples were preserved at −80° C. until their next use. The success of this first stage was confirmed by Western blot.

b) Test on calix-6-sulfonates

According to Example 1, grafting of the NHS plates was performed for 6 hours with a range of C6S diluted in a solution of 50 mM PBST. They were first saturated with a solution of 0.05% PBST milk 5% for 6 hours at ambient temperature. They were then washed three times with a solution of 0.05% PBST. The sample previously diluted in tris maleate was deposited on the plate and incubated one night at 2–8° C. The plate was then washed 6 times in 0.05%

PBST. The solution of developer antibody was incubated for 1 hour at ambient temperature. After a new series of washing, the streptavidine-PAL was incubated for 20 minutes. The plate was washed a last time before the deposit of PNPP (paranitrophenyl phosphate), that was incubated for 30 minutes at 37° C. The developer reaction was then stopped by the addition of soda.

Reading the DO was performed at 405 nm against a filter with 490 nm with the aid of a spectrophotometer.

c) Results

Figure 9:
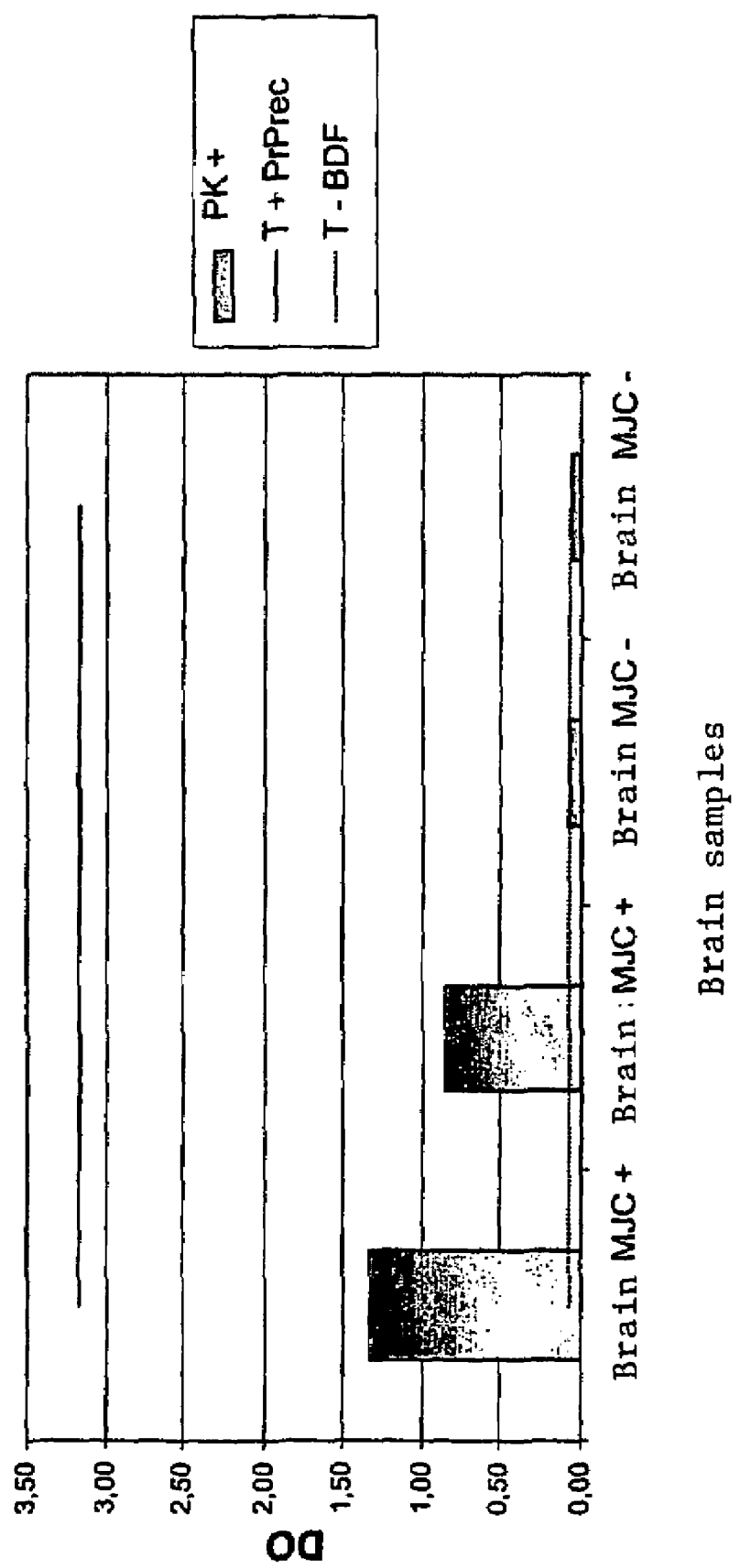
FIG. 9 shows a graphic representation giving the values of optical density (DO) obtained after placing calyx-arene C6S grafted on an activated amine plate (NHS) in contact with $PrP^{sc}$ extracted from the brains of patients affected or not affected with Creutzfeld-Jakob disease (MJC+/MJC−) by disclosure with the anti-PrP AC23 antibody marked with alkaline phosphatase.

The results are indicated in FIG. 9, that shows that the $PrP^{sc}$ of the samples from patients stricken with Creutzfeld-Jakob disease is surprisingly detectable by the process of the invention using a capture by C6S'es grafted on NHS plates and detection by an antibody directed specifically against the protein PrP, which is validated by the positive PrP recombinant human control and negative control PBST 0.05%.

EXAMPLE 6

Detection of $PrP^{sc}$ in LCR and Using C6S Grafted on a Solid Support 6.1 Preparation of Samples The specimens were constituted of samples of cerebrospinal fluid (LCR) that were preferably non-hemolyzed and without cellular debris. The samples were anonymous and preserved and frozen at −(80° C.) in tubes with walls that were slightly absorptive for proteins ("pre-lubricated micro centrifuge tube 1.7 ml", Marsh Biomedical Products, ref. T6050G).

They were divided into two categories:

Samples Positive for MJC.

These were postmortem LCR recovered during the autopsy by puncture in the cisterns and of which the research of the $PrP^{sc}$ in the cerebral tissue by Western blot permitted the confirmation of the diagnosis of MJC (certain cases). During autopsy, the LCR taken was immediately distributed into the tubes previously described without previous centrifugation (with the exception of samples having a significant amount of cellular debris) and the aliquots frozen at −80° C.

Samples Negative for MCJ. They are of 2 Types:

Postmortem LCR recovered during the autopsy and of which the research of the $PrP^{sc}$ in the cerebral tissue by Western blot permitted the elimination of the diagnosis of MJC (controls negative for MJC).

LCR of patients not afflicted with MJJ and stemming from external ventricular derivations (DVE). The storing conditions of the samples were identical to those previously described.

6.2 ELISA Approach a) Analytical Principle

The samples were simply incubated at an elevated temperature for a given time, then, after cooling, diluted to ½ or ⅕ in a buffer compatible with an immunometric analysis (ELISA) (tris maleate buffer pH 8). When the digestion by proteinase K occurred before depositing on plate C6S, the samples were digested by proteinase K for 15 minutes and then deposited on plate C6S without previous inhibition.

The term ELISA is employed even though the capture is not immunological because a reaction of the type ligand/refining agent with immunological development is concerned.

The ELISA techniques are immuno-enzymological quantitative techniques permitting the dosing of the investigated antigen by the transformation of a substrate into a soluble, measurable product proportional to the quantity of antigen present in the sample. The technique used here comprised the same steps as a non-competitive classical ELISA sandwich with the exception of the sensitizing of the cupules. In fact, the anti-prion capture antibody was replaced by the sulfonated calyx-6-arenes grafted on the NHS groups of the microplates by their amine function.

After immobilization of the C6S'es on the bottom of the cupules of a microplate and saturation of the non-specific sites for the fixation of the antigen, the sample was deposited and the plate incubated to permit bonding of the antigen to the C6S. Then, after several washings, the developer antibody specific for the prion protein and marked was added. The complexes formed were visualized by colorimetric method after the addition of the enzyme substrate, that is transformed into a colored product whose absorbency was determined with the aid of a microplate reader (automated spectrophotometer).

b) Mode of Operation

A volume of LCR was incubated in a dry stainless steel water pan at 75° C. for 15 minutes. After cooling, the sample was diluted 5 times in tris maleate buffer 0.2 M, pH 8 (addition of 4 volumes of buffer) and either deposited directly on a sensitized microplate in advance by the C6S'es or digested by proteinase K for 15 minutes at 37°, then deposited on microplate.

The successive stages of the immunometric analysis are enumerated below in chronological order:

1. Grafting the sulfonated calyx-6-arenes C6S'es on the activated amine plates (NHS) was performed in accordance with the method mentioned above for 6 hours at ambient temperature in accordance with a concentration range or in accordance with a fixed concentration, diluted in a solution of PBS 50 mM.

2. The plates were then washed 3 times in PBST 0.05%, then saturated in PBST 0.05% milk 5% for 1 hour at 37° C.

3. After washing, 100 ml LCR prepared in accordance with the analytical principle described above were deposited by sinks; the plates were incubated for 1:30 h at 37° C.

4. After washing, 100 ml of developer antibody was deposited by sinks (AC23-biotin at 0.5 µg/ml). The plates were incubated 1 h at ambient temperature.

5. After washing, the complexes formed are disclosed:

5.1 If the disclosure antibody was coupled to biotin, 100 ml of a solution of SA-PAL diluted to 1/20000 in PBST buffer 0.05% was deposited per sink. The plates were incubated 20 minutes at ambient temperature. After washing, 100 ml PNPP was deposited by sinks. The plates were incubated 10 to 30 minutes at 37° C. At the end of the incubation, the colorimetric reaction was stopped by addition of 50 ml NaOH at 0.4 N into each sink. The optical density was then measured by spectrophotometer with 405 nm against a filter with 450 nm.

5.2 If the disclosure antibody was coupled to peroxidase, 100 ml OPD was deposited by sinks. The plates were incubated 10 minutes in the dark and at ambient temperature.

At the end of the incubation, the colorimetric reaction was stopped by addition of 50 ml $H_2SO_4$ at 1.8 N into each sink. The optical density was then measured with a spectrophotometer with 495 nm.

b) Results

Figure 10:
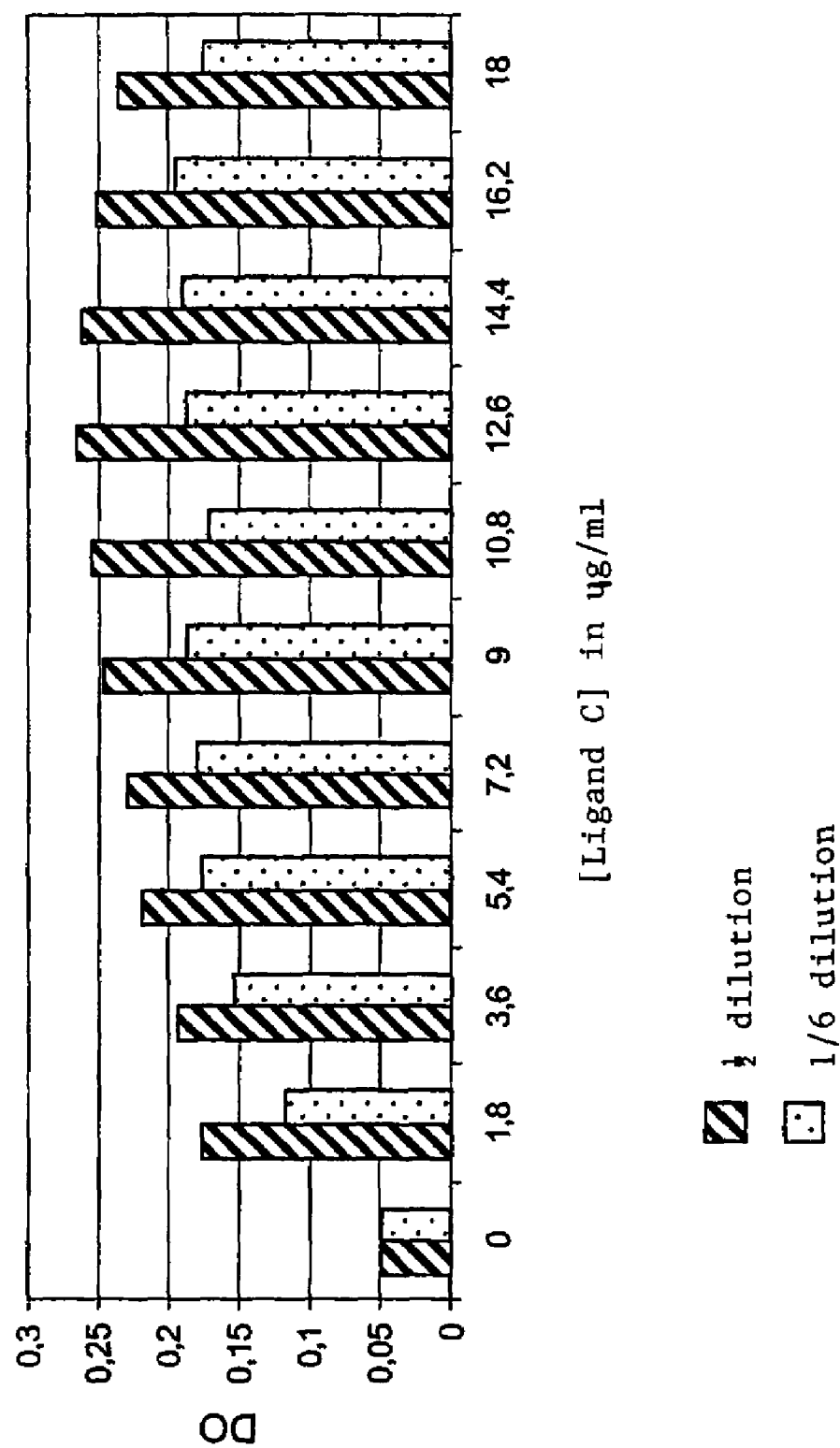
FIG. 10 shows a graphic representation giving the values of optical density (DO) obtained as a function of the concentration of calyx-arene C6S grafted onto an activated amine plate (NHS) after being placed in contact with a sample of LCR of the patient not affected with MJC, diluted at ½ or ⅙ and in the absence of digestion by proteinase K.

1. Verification of the Association of Sulfonated Monoamines calyx-6-arenes (C6S Grafted onto Microplate with the Protein Prion of Cerebrospinal Fluid (LCR):

A cerebrospinal fluid of the patient not afflicted with Creutzfeld-Jakob disease was heated 15 minutes and 75° C. and then diluted to one half or $1/6^{th}$ in a buffer compatible with an immunological disclosure in ELISA. The samples were not digested by proteinase K and thus deposited on a plate grafted with C6S'es in accordance with a concentration range comprised between 1.8 and 18 µg/ml. After incubation, the immunological disclosure of the antigen captured on the C6S'es was ensured by the antibody AC23 coupled with peroxidase, used at 0.5 µg/ml. The results are shown in FIG. 10.

These results show that the C6S'es enter readily into a combination with a form of protein prion in the LCR since a signal was observed from the first concentration of C6S'es immobilized at the bottom of the cupules.

2. Verification of the Association of the C6S'es with the Pathological Protein Prion in Heterogeneous Phase without Using Proteinase K:

An LCR of a patient not afflicted with MJJ (LCR−) and an LCR of a patient deceased from MCJ (MJC+) non-diluted or diluted to ½ undergo different types of heat treatment. They are then deposited on a plate grafted with the C6S'es at 7.2 µg/ml. After washing, the immunological disclosure was ensured by the antibody anti-prion AC23 coupled with biotin.

Figure 11:
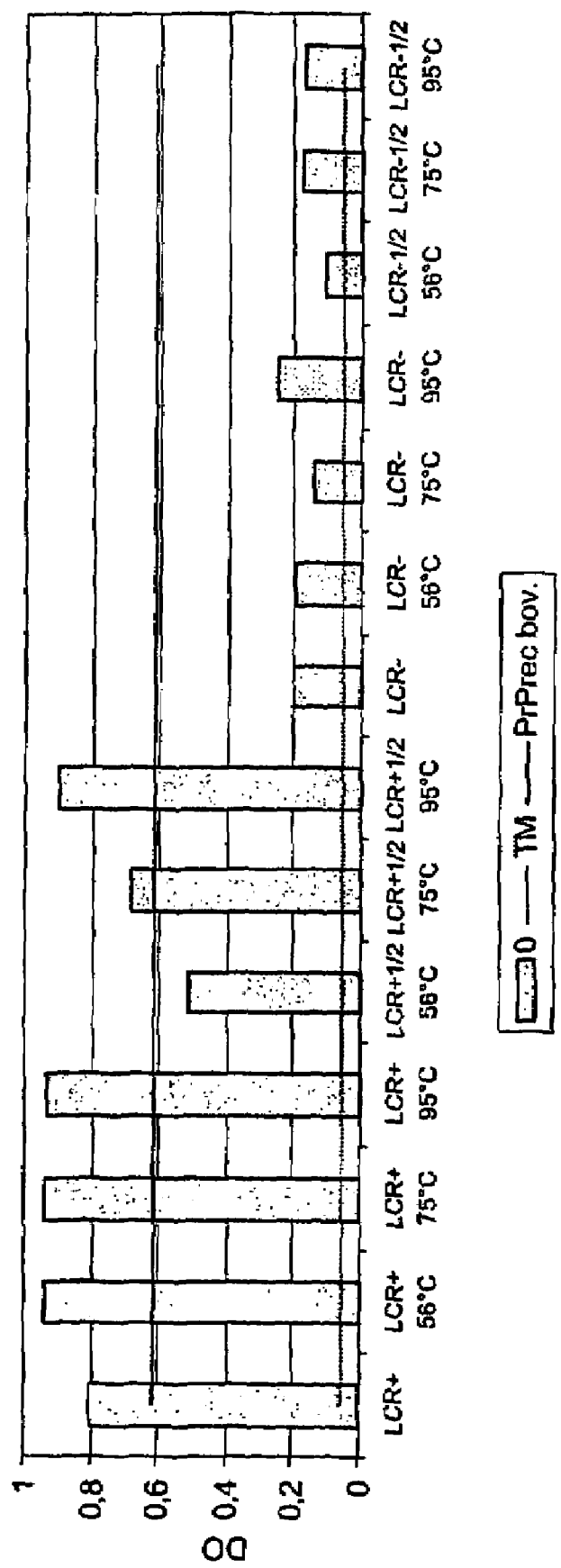
FIG. 11 shows a graphic representation giving the values of optical density (DO) obtained as a function of the concentration of calyx-arene C6S grafted onto an activated amine plate (NHS) after being placed in contact with a sample of LCR of the patients not affected with MJC (LCR−) or affected with this disease (LCR+), possibly diluted at ½ (LCR+½ or LCR−½) and in the absence of digestion by proteinase K.

The results are shown graphically in FIG. 11.

These results show an adsorption of the protein prion on the C6S'es grafted on the plate in the absence of treatment by proteinase K, more efficacious for the positive sample than for the negative sample. The different heat treatments slightly influence the efficacy of the adsorption of the protein prion on the C6S'es in the absence of dilution and, furthermore, when the sample is diluted. Thus, the test conditions favoring the adsorption of the protein prion on the MN C6S'es in heterogeneous phase appear to be a dilution of the samples and a treatment for 5 minutes at 95° C.

3. Verification of the Association of the C6S'es with the Pathological Protein Prion in Heterogeneous Phase with the Using of Proteinase K:

A stage of digestion by proteinase K was used for 15 minutes at 37° C. in pre-analytic treatment before capture on plate C6C on the digesting mixture for 1 hour at 37° C. The elimination of the residual proteinase K was ensured by successive washings in PBS Tween buffer 0.05%.

Figure 12:
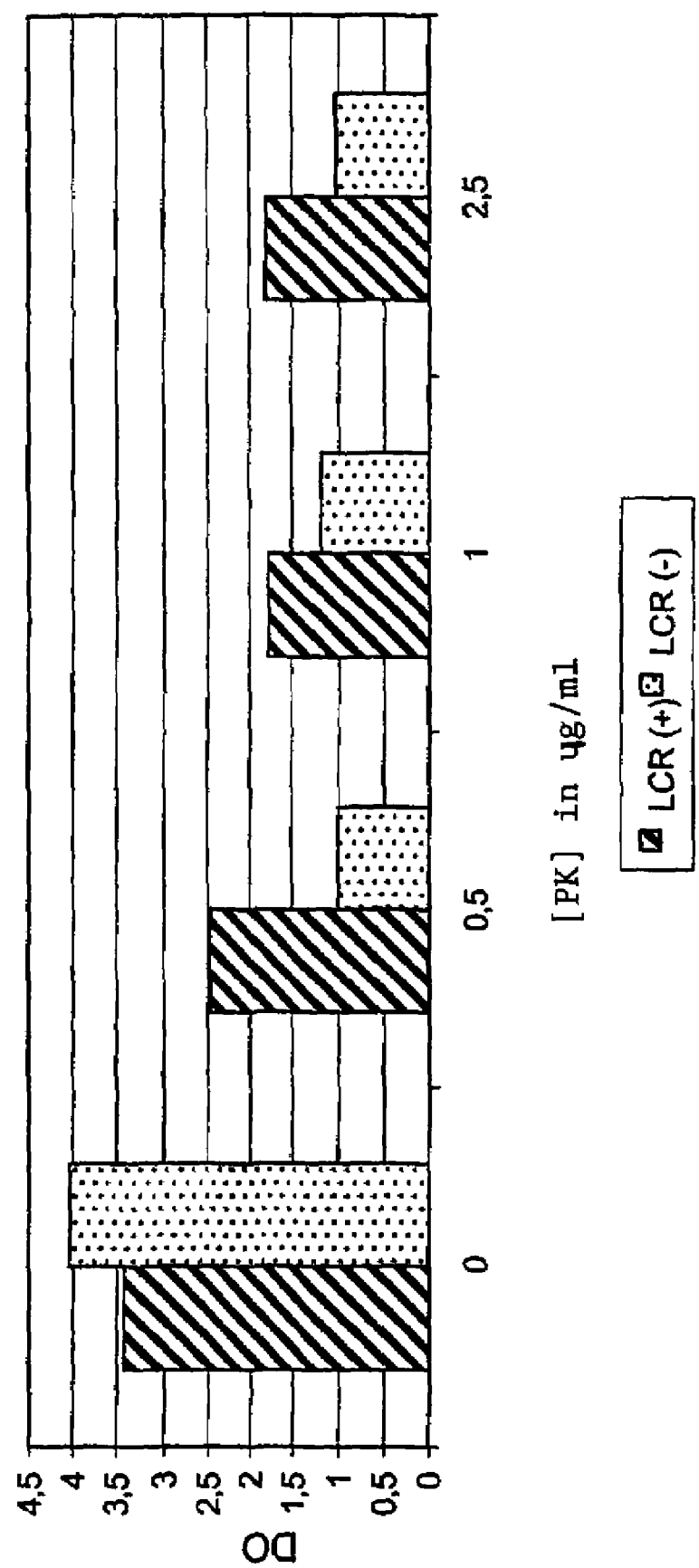
FIG. 12 shows a graphic representation giving the values of optical density (DO) obtained as a function of the concentration of proteinase K after placing calyx-arene C6S grafted onto an activated amine plate (NHS) in contact with a sample of LCR of patients not affected with MJC (LCR−) or affected with this disease (LCR+).

The results are indicated in FIG. 12.

These results show a difference of optical density in favor of the positive sample for MJC after digestion by proteinase K. The differential is visible from the first concentration of proteinase K tested (0.5 µg/ml).

d) Conclusion

Detection of the protein prion in the LCR is made possible in accordance with the invention. In fact, in the absence of digestion by proteinase K the detection of the total PrP (cellular and pathological) is amplified in the presence of the sulfonated calyx-6-arenes and, in an unexpected manner, the $PrP^{sc}$ is preferentially detected. The use of these C6S'es in capture after digestion of the samples by proteinase K permits the detection of the $PrP^{sc}$ of the LCR by furnishing a signal significantly different between the LCR stemming from patients not afflicted with MJC and the LCR stemming from patients affected with MJC.

The invention claimed is:

1. A process for detecting the presence of $PrP^{sc}$ in a biological sample, comprising:
    adding a macrocyclic adjuvant ligand (AML) that is free or linked to a support to the biological sample that may contain $PrP^{sc}$ to form a suspension;
    reacting the suspension with an anti-$PrP^{sc}$ antibody; and
    detecting anti-$PrP^{sc}$ antibody that is bound to $PrP^{sc}$ to identify the presence of $PrP^{sc}$ in the sample;
    wherein said AML is selected from the group consisting of metacyclophanes and veratrylenes.

2. The process according to claim 1, further comprises treating the biological sample with a proteinase K before or after contact with the AML to degrade PrP in the sample.

3. The process according to claim 1, wherein the biological sample is from an animal.

4. The process according to claim 3, wherein the sample is a tissue or cerebrospinal fluid or serum.

5. The process according to claim 1, wherein the solid support is functionalized by an NHS group or an $NH_2$ group and is a magnetic ball or a microplate.

6. The process according to claim 1, wherein the macrocyclic adjuvant ligand binds to $PrP^{sc}$ on sites that are contiguous or close in space, and on sites that bind to an antibody.

7. A process for detecting the presence of $PrP^{sc}$ in a biological sample, comprising:
    adding a macrocyclic adjuvant ligand (AML) that is free or linked to a support to the biological sample that may contain $PrP^{sc}$ to form a suspension:
    reacting the suspension with an anti-$PrP^{sc}$ antibody; and;
    detecting anti-$PrP^{sc}$ antibody that is bound to $PrP^{sc}$ to identify the presence of $PrP^{sc}$ in the sample,
    wherein the macrocyclic adjuvant ligand is a calyx-arene.

8. The process according to claim 7, wherein the calyx-arene is para-sulfonato-calyx-arenes functionalized on a phenolic face selected from the group consisting of p-sulfonato-calyx-[4]-arene, p-sulfonato-calyx-[6]-arene, p-sulfonato-calyx-[8]-arene or derivatives thereof.

9. The process according to claim 7, wherein the macrocyclic adjuvant ligand corresponds to the general formula (1) below, (I)

in which
    $R_1$ represents a hydrogen atom, a hydroxyl group, an OR group or an OCOR group with R as defined below,
    $R_2$ represents a hydrogen atom, a group R, COR, Pol, $CH_2Pol$ in which Pol represents a phosphate, sulfate, amine, ammonium, carboxylic acid group and R is as defined below,
    $R_3$ represents a hydrogen atom, a hydroxyl group, an OR group or an OCOR group in which R is as defined below, $R_4$ represents a hydrogen atom, a hydroxyl group, an OR group, an $OCH_2R$ group or an OCOR group in which R is as defined below, Y is an atom of carbon, nitrogen or an atom of sulfur, $R_5$ and $R_6$ are, each independently, absent or represent a hydrogen atom, a $CH_2$ group or R as defined below, or $R_5$ and $R_6$ together represent an atom of oxygen or of sulfur, X represents a $CH_2$ group or an atom of oxygen or of sulfur, m represents a positive integer equal to 0 or 1, R represents a hydrogen atom or a hydrocarbon chain, saturated or unsaturated, branched or unbranched, cyclic or non-cyclic, substituted or not substituted by a halogen group and carrying polar or non-polar functions, n is a positive integer between 3 and 15, and $R_1$ to $R_5$, R, X, Y and m can be different.

* * * * *